United States Patent
Jeong et al.

(10) Patent No.: US 12,059,309 B2
(45) Date of Patent: Aug. 13, 2024

(54) BIOSIGNAL MEASURING DEVICE FOR CONVERTING AND TRANSMITTING BIOSIGNAL AND METHOD OF PROCESSING THE BIOSIGNAL

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Soo A Lim, Seoul (KR)

(73) Assignee: ATSENS CO., LTD., Gyeonggi-do (KR)

( * ) Notice: Subject to any disclaimer, the term of this patent is extended or adjusted under 35 U.S.C. 154(b) by 117 days.

(21) Appl. No.: 17/232,935

(22) Filed: Apr. 16, 2021

(65) Prior Publication Data
US 2022/0330924 A1 Oct. 20, 2022

(51) Int. Cl.
| A61B 8/00 | (2006.01) |
| A61B 8/08 | (2006.01) |
| H04W 72/08 | (2009.01) |
| H04W 72/542 | (2023.01) |
| H04W 76/10 | (2018.01) |

(52) U.S. Cl.
CPC ............ *A61B 8/565* (2013.01); *A61B 8/0883* (2013.01); *H04W 72/542* (2023.01); *H04W 76/10* (2018.02)

(58) Field of Classification Search
CPC ... A61B 8/565; A61B 8/0883; H04W 72/085; H04W 76/10
See application file for complete search history.

(56) References Cited

U.S. PATENT DOCUMENTS

| 4,870,685 | A | * | 9/1989 | Kadokawa | ........... H03M 7/3053 375/241 |
| 6,269,086 | B1 | * | 7/2001 | Magana | ............ H04W 52/0225 370/280 |
| 9,197,902 | B2 | | 11/2015 | Mazumdar et al. | |

(Continued)

FOREIGN PATENT DOCUMENTS

| CN | 111067509 B | | 10/2022 | |
| EP | 1972268 | * | 9/2008 | ............... A61B 5/00 |

(Continued)

OTHER PUBLICATIONS

Office Action issued in corresponding JP Application No. 2021-069562, issued May 24, 2022, 2 pages.

(Continued)

*Primary Examiner* — Alexei Bykhovski
(74) *Attorney, Agent, or Firm* — Guntin & Gust, PLC; Miyoung Shin

(57) ABSTRACT

A biosignal measuring apparatus for converting and transmitting biosignals, includes a sensing unit configured to sense a user's electrocardiogram data, a communication unit configured to establish a wireless channel with a data receiving device, and a processing unit configured to determine real-time transmission characteristics based on communication quality information regarding the wireless channel, to determine a data resolution corresponding to the real-time transmission characteristics, to convert the electrocardiogram data according to the data resolution, and to transmit the electrocardiogram data to the data receiving device.

12 Claims, 12 Drawing Sheets

(56) References Cited

U.S. PATENT DOCUMENTS

| | | | |
|---|---|---|---|
| 9,717,412 B2 | 8/2017 | Roham et al. | |
| 10,881,315 B2 | 1/2021 | Kuwabara et al. | |
| 2005/0249239 A1* | 11/2005 | Pierce | G16H 40/67 370/466 |
| 2015/0350939 A1* | 12/2015 | Sakazume | H04N 21/238 455/550.1 |
| 2016/0022161 A1 | 1/2016 | Khair | |
| 2017/0224244 A1* | 8/2017 | Kuwabara | A61B 5/0006 |

FOREIGN PATENT DOCUMENTS

| | | |
|---|---|---|
| EP | 1972268 A1 | 9/2008 |
| KR | 1020060079527 A | 7/2006 |
| KR | 1020130012903 | 2/2013 |
| KR | 101308522 B1 | 9/2013 |
| KR | 1020130106865 | 9/2013 |
| KR | 1020140035313 A | 3/2014 |
| KR | 1020140128847 | 11/2014 |
| KR | 101890072 B1 | 8/2018 |
| WO | 2016024495 A1 | 2/2016 |

OTHER PUBLICATIONS

Office action issued to corresponding Korean Application No. 1020190157685, issued Feb. 26, 2021.

Notice of Final Rejection issued to corresponding Korean Application No. 1020190157685, issued Aug. 25, 2021, with an English translation thereof, 6 pages.

Notice of Refusal of Counterpart Japanese Application No. 2021-069562 and English translation (total seven (7) pages) mailed Sep. 27, 2022.

\* cited by examiner

BIOSIGNAL MEASURING DEVICE FOR CONVERTING AND TRANSMITTING BIOSIGNAL AND METHOD OF PROCESSING THE BIOSIGNAL

BACKGROUND

1. Field

One or more embodiments relate to a biosignal measuring apparatus in which biosignals are converted into a data resolution determined by considering transmission characteristics of a wireless channel, and a method of processing biosignals.

2. Description of the Related Art

In order to maintain human life, it is required that blood pumped by heart beats flows along the arteries throughout the body without any blockage, and then returns to the heart through the veins. In this manner, oxygen and nutrients are supplied to each tissue of the body and waste consumed through metabolism can be removed.

However, if the blood is not delivered to a specific part of the body properly due to poor cardiac status, or if a clot or embolus is generated in the blood rendering the blood turbid, capillaries of a certain tissue of the body may become blocked causing tissue necrosis, etc., which can be life threatening. Therefore, in addition to clinical consultations, imaging examinations, etc. are used to examine cardiac abnormalities, and as a method of early diagnosis, measuring an electrocardiogram and presenting the measured electrocardiographic signals in a graphic form is also widely used to diagnose cardiac abnormalities of patients.

An electrocardiogram refers to a graphical recording of potential changes on the body surface which appears in accordance with mechanical activities of heart beats, such as shrinking or expansion of cardiac muscle, and is a non-invasive examination that is not only simple to measure, but reproducible, easy to record repeatedly, and inexpensive. It is widely used to diagnose arrhythmia and coronary artery disease (an arterial disease of the heart) and to observe progress of patients with heart disease.

In general, electrocardiograms are measured by attaching electrocardiogram measurement sensors onto the upper left and right portions of the chest as well as the lower left and right portions of the chest, and then using potential differences sensed according to the positions of each sensor.

SUMMARY

One or more embodiments according to the teachings of the present disclosure include a biosignal measuring apparatus for converting electrocardiogram data in accordance with a data resolution corresponding to communication environments and transmission characteristics, a measurement method, and a computer program.

Additional aspects will be set forth in part in the description which follows and, in part, will be apparent from the description, or may be learned by practice of the presented embodiments of the disclosure.

According to one or more embodiments, a biosignal measuring apparatus for converting and transmitting biosignals includes: a sensing unit configured to sense user's electrocardiogram data; a communication unit configured to establish a wireless channel with a data receiving device; and a processing unit configured to determine real-time transmission characteristics based on communication quality information regarding the wireless channel, to determine a data resolution corresponding to the real-time transmission characteristics, to convert the electrocardiogram data according to the data resolution, and to transmit the electrocardiogram data to the data receiving device.

In at least one variant, the processing unit may determine current transmission characteristics including wireless bandwidths or radio frequency (RF) communication quality based on communication quality information regarding the wireless channel.

In another variant, the processing unit may convert biosignals by determining a data resolution including a transmission data size in consideration of real-time transmission characteristics with the receiving device, and wavelet transforming electrocardiogram data k times according to the transmission data size.

In further another variant, if a transmission delay is detected under current transmission characteristics by using feedback signals from the data receiving device, the processing unit may determine a data resolution to be applied to the electrocardiogram data considering the scale of the transmission delay, and convert the electrocardiogram data according to the data resolution.

In another variant, the transmission delay may be calculated by comparing a transmission time of the electrocardiogram data generated by the processing unit and a transmission completion time received from the data receiving device.

In another variant, the processing unit may recompress a certain section data of the converted electrocardiogram data and transmit the section data to the receiving device. The processing unit may store sensed electrocardiogram data without conversion in an internal memory.

According to one or more embodiments, a biosignal measuring apparatus for converting and transmitting biosignals includes: a sensing unit configured to sense electrocardiogram data; a communication unit configured to establish a wireless channel with a data receiving device; and a processing unit configured to convert, when receiving communication control signals from the data receiving device via the wireless channel, a data section designated by the communication control signals into a set value corresponding to the communication control signals, and to transmit the data section.

In at least one variant, the processing unit may convert, when the communication control signals further include an output scale based on a user input, a data section designated by the communication control signals in consideration of the output scale included in the communication control signals.

In another variant, the processing unit may extract biometric parameters included in the communication control unit to designate a data section using the said biometric parameters, and convert the data section into a set value included in the communication control unit.

According to one or more embodiments, a method of measuring biosignals for converting and transmitting the same includes: sensing of a user's electrocardiogram data by the biosignal measuring apparatus; establishment of a wireless channel with a data receiving device by means of the biosignal measuring apparatus; determining real-time transmission characteristics based on communication quality information regarding the wireless channel, determining a data resolution corresponding to the transmission characteristics, and converting the electrocardiogram data according to the data resolution, by means of the biosignal measuring apparatus; and transmission, by the biosignal measuring apparatus, of the electrocardiogram data to the data receiving device.

In at least one variant, the converting of electrocardiogram data may include determining the real-time transmission characteristics including wireless bandwidths or RF communication quality based on communication quality information regarding the wireless channel.

In another variant, the converting of electrocardiogram data may include determining the data resolution including a transmission data size in consideration of transmission characteristics with the receiving device, and wavelet-transforming the electrocardiogram data k times according to the transmission data size.

In further another variant, when generation of transmission delay is detected under current transmission characteristics, using feedback signals from the data receiving device, the converting of electrocardiogram data may include determining a data resolution to be applied to the electrocardiogram data in consideration of the scale of the transmission delay, and converting the electrocardiogram data according to the data resolution.

In another variant, the transmission delay may be calculated by comparing a transmission time of electrocardiogram data generated by the processing unit and a transmission completion time received from the data receiving device.

In another variant, the converting of electrocardiogram data may include recompressing some section data of the electrocardiogram data.

In another variant, the converting of the electrocardiogram data may include storing the electrocardiogram data in an internal memory.

According to one or more embodiments, a method of measuring biosignals includes: sensing of a user's electrocardiogram data by a biosignal measuring apparatus; establishment of a wireless channel with a data receiving device by the biosignal measuring apparatus; when the biosignal measuring apparatus receives communication control signals from the data receiving device via the wireless channel, converting a data section designated by the communication control signals into a set value corresponding to the communication control signals; and transmitting the data section converted by the biosignal measuring apparatus.

In at least one variant, the conversion may include, when the communication control signals include an output scale based on a user input, converting a data section designated by the communication control signals in consideration of the output scale included in the communication control signals.

In another variant, the conversion may include extracting biometric parameters included in the communication control unit, designating a data section using the biometric parameters, and converting the data section to a set value included in the communication control unit.

According to one or more embodiments, a computer program is stored in a medium to execute any one of the methods according to embodiments by using a computer.

In addition to the above, other methods and systems for implementing the present disclosure, and computer readable recording media for recording a computer program for executing the methods are further provided.

Other aspects, features, and advantages besides those described above will become apparent from the following drawings, claims, and detailed description of the invention.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 6A is a diagram illustrating biosignals received from the biosignal measuring apparatus;

FIG. 6B is a diagram illustrating expanding TI section in the biosignals of user input; and FIG. 6C is a diagram illustrating generating and transmitting data to the data receiving device;

DETAILED DESCRIPTION

Figure 1:
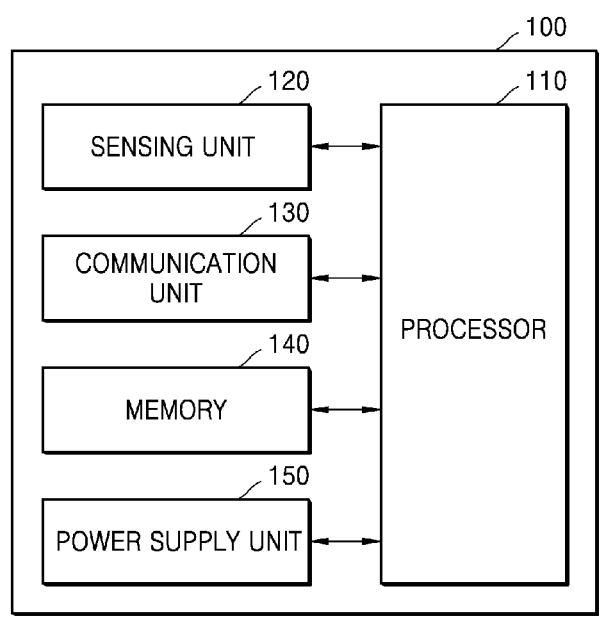
FIG. 1 is a block diagram of a biosignal measuring apparatus according to embodiments of the disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A data conversion unit may store electrocardiogram data in a local memory without conversion. Further, the terms such as "include" or "have" in various embodiments of the present disclosure are used to specify the existence of features, numbers, processes, operations, components, parts recited in the detailed description, or combinations thereof, and thus should not be understood as pre-excluding the existence or possibility for addition of one or more other features, numbers, processes, operations, components, parts, or combinations thereof.

In various embodiments of the present disclosure, expressions such as "or," etc. include any and all combinations of the words listed along with the term. For example, "A or B" may indicate including A only, B only or both A and B.

Expressions such as "1st," "2nd," "first" or "second" used in several embodiments of the present disclosure may modify diverse components of various embodiments, but are not used to limit the said components. For example, the expressions do not limit the order and/or importance of the said components. The aforementioned expressions may be used to distinguish one component from other components. For example, both of the first user device and the second user device are all user devices; however, the foregoing user devices indicate each different user device. For example, the first component may also be named as the second component, and similarly, the second component may be named as the first component within the extent of right claimed by embodiments of the present disclosure.

When a certain component is described as "being joined" or "being connected" with other components, the said component may be joined or connected directly with other components; however, such expressions should be understood to the effect that a third component may exist therebetween. On the contrary, when a certain component is described as "being directly joined" or "being directly connected" with other components, it should be construed that no other component is placed therebetween.

In embodiments of the present disclosure, terms such as "module," "unit," "part," and the like are used to refer to the components that perform at least one function or operation, and these components can be implemented by means of hardware or software, or by combining hardware and software. In addition, multiple "modules," "units," and "parts" can be integrated into at least one module or chip, and thus be implemented by at least one processor unless each of them is required to be implemented individually by specific hardware.

Terms in various embodiments of the present disclosure are used to describe a specific embodiment only, and are not intended to limit various embodiments of the present disclosure. Expressions in the singular form represent their plural forms as well unless the context shows a clear difference in meaning.

Unless otherwise defined, all terms used herein, including technical or scientific terms, have the same meanings as generally understood by a person with ordinary skill in the art to which various embodiments of the present disclosure pertain.

As for the general terms defined in common dictionaries, they should be construed as having the same meaning as their contextual meanings in light of related technologies, and shall not be interpreted into ideal or excessively formal meanings unless explicitly defined in various embodiments of the present disclosure.

Hereinafter, various embodiments of the present disclosure will be described in detail referring to the attached drawings.

In the present description, biosignals refer to signals including data on a body temperature, pulse, electrocardiogram, brain wave, respiration rate, step count, stress, hormone, level of exercise, amount of calorie consumed, body fat, total body fluid, blood glucose value, blood pressure, etc.

FIG. 1 is a block diagram of a biosignal measuring apparatus 100 according to embodiments of the present disclosure.

The biosignal measuring apparatus 100 may include a processor 110, a sensing unit 120, a communication unit 130 and a memory 140 to process electrocardiogram data according to a process mode and/or a process method determined based on a receiving device.

The biosignal measuring apparatus 100 may refer to an apparatus for measuring biosignals of humans, animals, etc. The biosignal measuring apparatus 100 may be equipped on an object in a non-invasive or invasive manner to measure electrocardiogram according to the heartbeats of the object. In some forms, the biosignal measuring apparatus 100 may be implemented in a form that can be attached onto the skin or body of the object, but not limited to this, it may also be implemented in various manners. Here, an object may be, but not limited to, a human, animal, or body parts of a human or animal such as chest, and any others from which electrocardiogram can be sensed or measured are deemed as an object. In addition, an electrocardiogram refers to a graphical recording of potential changes which appear on body surfaces in accordance with mechanical activities of heart beats, such as shrinking or expanding of cardiac muscles, and the expression of "sensing electrocardiogram" shall be construed as having the same meaning as "sensing potential changes" generated on the body surface of the object according to its heart beats.

The processor 110 may process biosignals of an object by being electrically connected to the sensing unit 120, the communication unit 130, and the memory 140. The processor 110 may transmit electrocardiogram data sensed by the sensing unit 120 to an external electronic device. In one form, the processor 110 may convert electrocardiogram data to reduce power consumption in consideration of the capacity of power supply of the biosignal measuring device 100. Additionally, or alternatively, the processor 110 may convert electrocardiogram data to adjust the size of transmission data in consideration of transmission characteristics. The processor 110 may transmit converted electrocardiogram data to an external receiving device. The processor 110 may include detailed components as described in FIG. 2.

The sensing unit 120 may be attached onto the body of an object in an invasive or non-invasive manner to sense electrocardiogram data of the object. The sensing unit 120 may measure electrocardiogram data from one or more channels by means of multiple electrodes. The sensing unit 120 may receive electrocardiogram data measured by electrically connected electrodes from one or more channels.

The communication unit 130 is a device for transmission and reception of data with other electronic devices via communications network. The communication unit 130 is a device for transmitting and receiving data via a wireless network or a wired network. The communication unit 130 may transmit and receive data by processing the data according to communication control signals of the processor 110. The communication unit 130 may establish a wireless channel with a data receiving device (200 of FIG. 6).

The memory 140 may store biosignals including electrocardiogram data, etc. sensed by the sensing unit 120. The memory 140 may store a program for processing and control of the processor 110. The memory 140 may store data transmitted and received via the communication unit 130. The memory 140 may store electrocardiogram data generated by the processor 110, information on cardiac status of an object, etc. The memory 140 may store biosignals including measured electrocardiogram data, etc. without conversion.

The power supply unit 150 may supply power to the processor 110, the sensing unit 120, the communication unit 130, and the memory 140. The power supply unit 150 may be implemented in a rechargeable manner, allowing a detachable form. The power supply unit 150 may supply power within a predetermined capacity to the processor 110, the sensing unit 120, the communication unit 130, and the memory 140. The power supply unit 150 may be charged by power supply from an external power supply device within a power supply capacity.

In FIG. 1, it is described that the processor 110 and the sensing unit 120 are provided in one device; however, the processor 110 and the sensing unit 120 may be provided and implemented in each separate device. In such case, the processor 110 and the sensing unit 120 may be connected electrically or via communications network.

Figure 2:
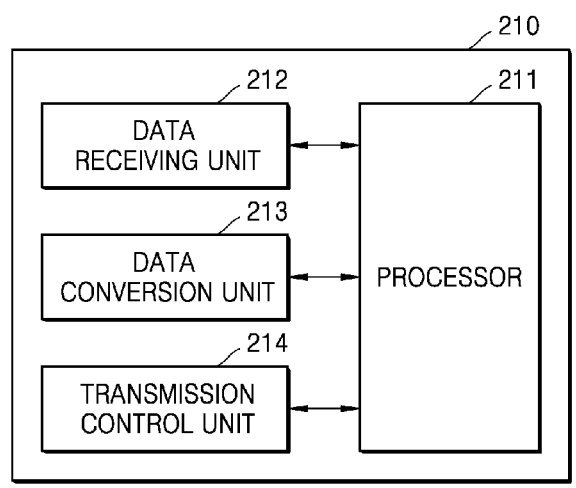
FIG. 2 is a block diagram of a processing unit according to embodiments of the present disclosure.

The processor 110 in FIG. 1 may be implemented by being substituted with the processing unit 210 in FIG. 2. In this case, the processing unit 210 and the sensing unit 120 may be provided inside the bio-signal measuring apparatus 100.

In another embodiment, the processing unit 210 may be implemented in a separate device from the bio-signal measuring apparatus 100. The processing unit 210 and the bio-signal measuring device 100 may be provided and implemented in separate devices. In this case, the processing unit 210 and the bio-signal measuring apparatus 100 may be electrically connected or connected through a communication network.

FIG. 2 is a block diagram of a processing unit 210 according to embodiments of the present disclosure.

The processing unit 210 may be implemented in the biosignal measuring device 100, an external data receiving device 200, or other electronic device. The processing unit 210 may be implemented to be included in the biosignal measuring device 100 and the external data receiving device 200, respectively.

The processing unit 210 may include a processor 211, a data receiving unit 212, a data conversion unit 213, and a transmission control unit 214. The processing unit 210 may be implemented as shown in 110 of FIG. 1 inside the biosignal measuring device, or may be implemented inside of an external device (200 of FIG. 7).

The processor 211 is a component for overall control of the processing unit 210 and may include one or more processors.

For example, the processor 211 may include a CPU, RAM, ROM, and system bus. In this regard, a ROM is a component in which instruction sets for system booting process are stored, and a CPU copies an operating system (O/S) stored in the biosignal measuring apparatus 100 to a RAM according to the instruction sets stored in the ROM, and executes the O/S for booting the system. Once the booting process is completed, the CPU may copy some stored applications to the RAM, and execute them to perform various operations. Although the biosignal measuring apparatus 100 is described as having one CPU in the above explanation, it may be implemented by multiple CPUs (or DSP, separate functional blocks, etc.).

The processor 211 may be implemented by a digital signal processor (DSP), a microprocessor, and a time controller (TCON). However, not limited to the above, it may include one or more from a central processing unit (CPU), micro controller unit (MCU), micro processing unit (MPU), controller, application processor (AP), communication processor (CP), and ARM processor, or may be defined by corresponding terms. In addition, the processor 211 may be implemented by a System on Chip (SoC) and a large scale Integration (LSI) with embedded processing algorithms, or in the form of field programmable gate array (FPGA).

The data receiving unit 212 may receive data sensed by the sensing unit 120. The data receiving unit 212 may receive electrocardiogram data through an electric line. The data receiving unit 212 may receive electrocardiogram data in a wireless or wired manner.

The data conversion unit 213 may wavelet transform electrocardiogram data received from the sensing unit 120. The data conversion unit 213 may determine real-time transmission characteristics based on communication quality information regarding the data receiving device and the wireless channel, and may further determine a data resolution corresponding to the real-time transmission characteristics. The data conversion unit 213 may convert biosignals, for example, electrocardiogram data in accordance with a data resolution corresponding to transmission characteristics. Characteristics of physical layer are a representative example of factors determining the communication quality. Normally, communication quality information may include RF signal strength. Also, communication quality information may include information on time-variant and band-limitation characteristics which vary frequently, frequency selectivity, modulation mode allowing wider bandwidth with less power consumption, delay dispersion information, Doppler spread information, etc.

The data conversion unit 213 specifies the first correction scale or the first translation degree through a data resolution corresponding to real-time transmission characteristics, and may wavelet transform biosignals including electrocardiogram data, etc. according to the first correction scale or the first translation degree. At this time, the biosignals, such as electrocardiogram data, etc. can be decomposed into multiple frequency components. Further, the data conversion unit 213 may decompose biosignals including electrocardiogram data, etc. into a plurality of data sections, and each of a plurality of data sections can be converted into a bit scale. A bit scale may be determined by a pattern of the corresponding section.

The data conversion unit 213 may designate the first bandwidth through a data resolution corresponding to transmission characteristics, and convert biosignals including electrocardiogram data, etc. to raise, among the components of biosignals such as electrocardiogram data, etc., the resolution of the first bandwidth, and lower the resolution of the rest of the bandwidths, i.e., the second bandwidth. At this time, wavelet transformation may be used as a transformation method; however, it is not limited to the wavelet transformation, and various other methods are also available. In this case, biosignals such as electrocardiogram data, etc. can be decomposed into a plurality of frequency components based on bandwidths. Further, the data conversion unit 213 may decompose biosignals including electrocardiogram data, etc. into a plurality of data sections, and each of a plurality of data sections can be converted into a bit scale. The bit scale may be determined by a pattern of the corresponding section.

The data conversion unit 213 may decompose biosignals including electrocardiogram data, etc. into multiple data sections based on frequency components, data size, time intervals, etc. before converting the biosignals by applying a data resolution.

The data conversion unit 213 may measure whether a transmission delay is generated at the time of transmission of electrocardiogram data, and transmission characteristics including quality of a wireless channel (e.g. available wireless bandwidth, RF communication quality, etc.) through communication quality information regarding the wireless channel. The data conversion unit 213 may determine a data resolution which enables transmission of biosignals without any data loss under transmission characteristics of a wireless channel. On this occasion, generation of transmission delay may be determined by feedback signals from the data receiving device 200. Further, the feedback signals may be received from the data receiving device 200, or obtained through the wireless channel with the data receiving device

200. Here, the feedback signal may be obtained via a wireless channel between the measuring device 100 and the data receiving device 200. The feedback signal may include a reception time, a transmission time, a reception rate, a transmission rate, and the like of transmitted/received data.

The data conversion unit 213 can reduce the data size or capacity of electrocardiogram data transmitted to the wireless channel through the conversion. As the size of transmission data decreases, the electrocardiogram data can be transmitted without time delay to the external data receiving device 200 in an environment in which a transmission delay occurs. In another embodiment, the data conversion unit 213 may convert biosignals such as electrocardiogram data, etc. according to communication control signals from the external data receiving device 200. The data conversion unit 213 may calculate a set value corresponding to the communication control signals including output scales (e.g. image resolution, etc.) of the data receiving device, and convert biosignals including electrocardiogram data, etc. by applying a set value corresponding to the communication control signals. At this time, a section where the aforementioned set value corresponding to the communication control signals is applied may be a part of the biosignals including electrocardiogram data, etc. designated by the communication control signals. The communication control signal may include information related to communication setting of the electrocardiogram data, and may include information for applying different communication settings for each predetermined section in relation to the electrocardiogram data. The communication control signals may include an output scale value (i.e. image resolution value) based on a user input entered in the data receiving device or a section designated by user input. The set value may include a data resolution of biosignals such as electrocardiogram data, etc. The data resolution can be determined individually by section. The data resolution is related to the accuracy and sensitivity of data, and data with high resolution may be data with high accuracy and sensitivity and high capacity, and data with low resolution may be data with low accuracy, sensitivity and small capacity. Different data resolutions may be applied to the section requiring higher sensitivity and the section requiring lower sensitivity.

In another embodiment, the communication control signals may include biometric parameters. The data conversion unit 213 may designate a data section using biometric parameters, and convert the designated data section by applying a set value included in communication control signals. In such case, the data section designated based on biometric parameters may be a section in which abnormal biosignals are sensed, a section showing an abnormal heart rate, or a section in which an abnormal P wave is detected.

In another embodiment, the data conversion unit 213 may convert electrocardiogram data considering status information on the power supply unit 150, status information on the data receiving device 200, etc. The data conversion unit 213 may convert biosignals such as electrocardiogram data, etc. into a smaller transmission data size if the remaining capacity of the power supply unit 150 is lower than a predetermined minimum capacity value. When the size of transmission data decreases, the power required for transmitting a single transmission unit for one time can be reduced, based on the transmission unit of electrocardiogram data. For example, the data conversion unit 213 may increase or decrease the transmission data size of electrocardiogram data under transmission characteristics with the receiving device, e.g., communication protocol at the time of transmission, version of communication protocol, type of communication network, transmission characteristics, transmission speed, time delay due to specification or performance of the receiving device 200, or delay-generating environment.

The data conversion unit 213 may convert electrocardiogram data considering transmission characteristics, status information on the power supply unit 150, status information on the data receiving device 200, etc.

The data conversion unit 213 may store electrocardiogram data in a local memory without conversion. After storing the data in a local memory, the data conversion unit 113 may perform a converting process for transmission to a remote device.

The data conversion unit 213 may obtain a transmission time of electrocardiogram data and transmission completion time of the same in consideration of feedback signals from the data receiving device, then generate transmission delay information by comparing the aforementioned transmission time and transmission completion time of electrocardiogram data, and detect generation of transmission delay considering the transmission delay information. The transmission time may include information regarding the point of time when the electrocardiogram data is transmitted to the data receiving device 200. The transmission completion time may include information regarding the time measured by the data receiving device 200 when the electrocardiogram data is transmitted.

The electrocardiogram data may be converted into a transmission data size, and thus converted into one or more transmission data. As such, the transmission data may be transmitted to one wireless channel, or can be transmitted to multiple wireless channels in a parallel or serial manner.

To enhance transmission efficiency, the biosignal measuring apparatus 100 may compress the electrocardiogram data.

The transmission control unit 214 may transmit transmission data of electrocardiogram data converted by the data conversion unit 213 to a designated data receiving device 200. The transmission control unit 214 may transmit one or more transmission data selected from transmission data of electrocardiogram data processed by the data conversion unit 213.

Figure 3:
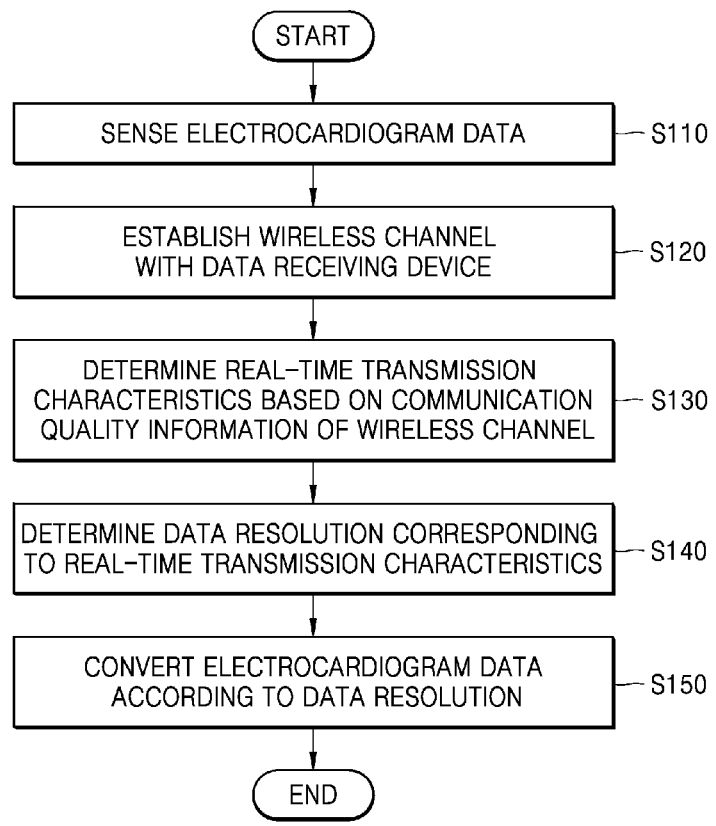
FIG. 3 is a flowchart of a biosignal processing method according to one embodiment of the present disclosure.
Figure 4:
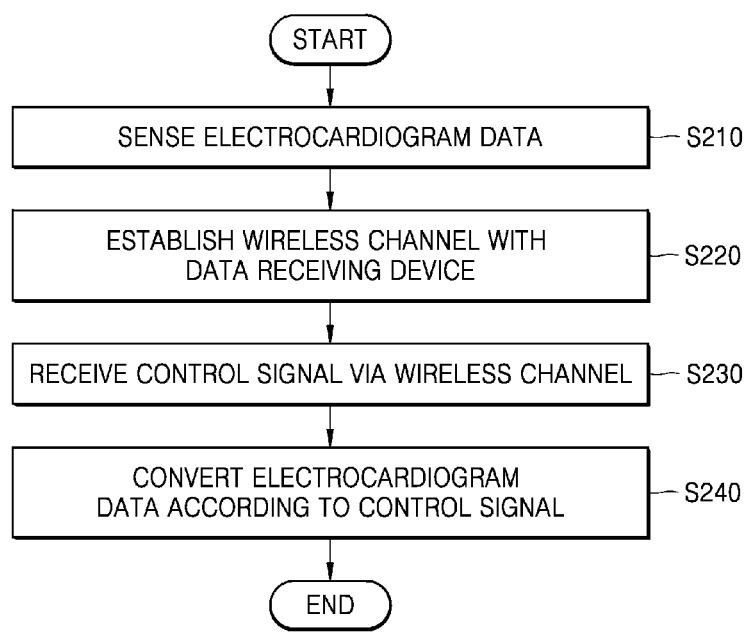
FIG. 4 is a flowchart of a biosignal processing method according to another embodiment of the present disclosure.
Figure 5:
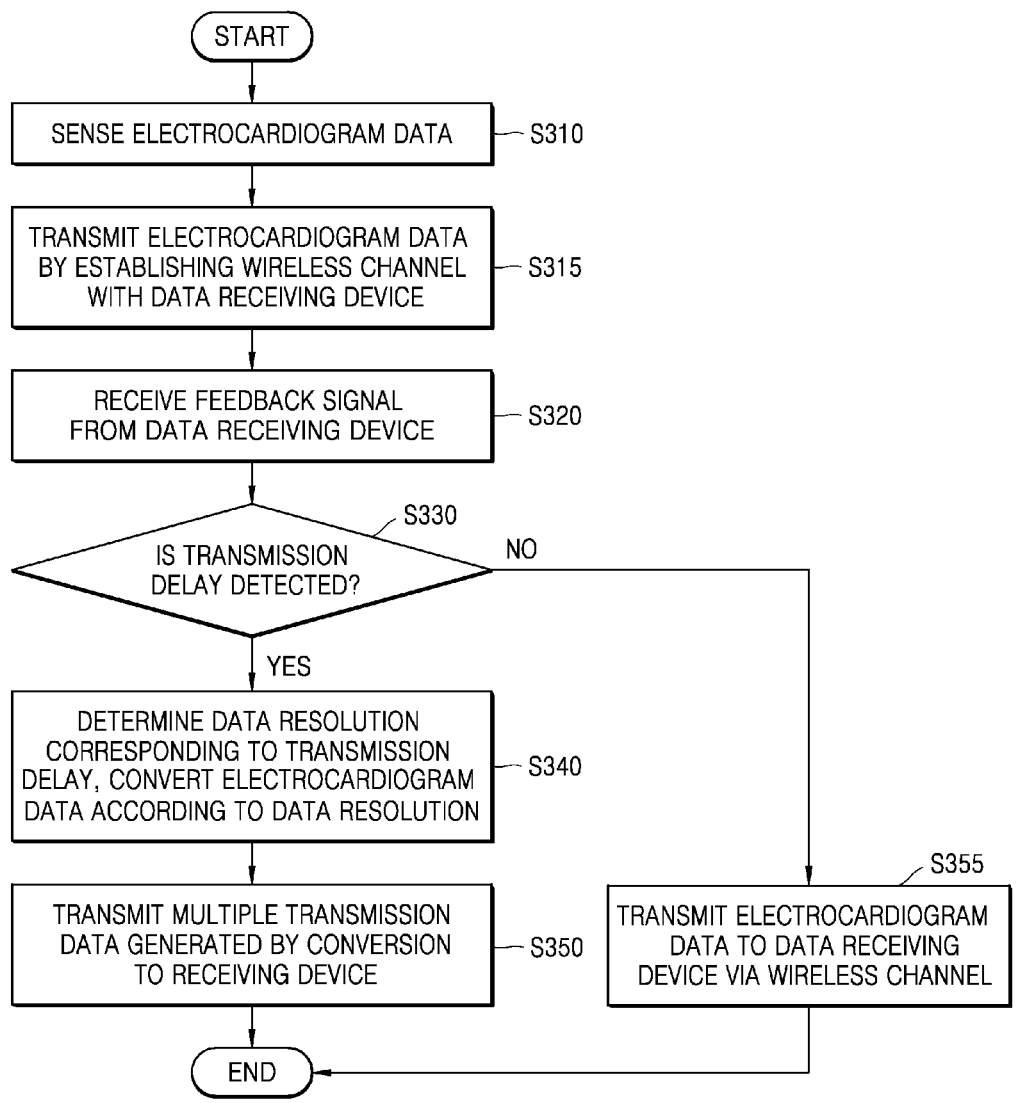
FIG. 5 is a flowchart of a biosignal processing method according to further another embodiment of the present disclosure.

FIGS. 3 to 5 are flowcharts of biosignal processing method according to embodiments of the present disclosure. FIG. 3 illustrates a flowchart that converts electrocardiogram data according to data resolution.

The biosignal measuring apparatus 100 may transmit sensed electrocardiogram data to an external receiving device at a predetermined time interval.

In Operation S110, the biosignal measuring apparatus 100 may sense electrocardiogram data.

In Operation S120, the biosignal measuring apparatus 100 may establish a wireless channel with the data receiving device 200.

In Operation S130, the processing unit 210 may determine current transmission characteristics real-timely based on communication quality information regarding the wireless channel. The data conversion unit 213 may measure whether a transmission delay is generated at the time of transmission of electrocardiogram data, and transmission characteristics including quality of a wireless channel (e.g. available wireless bandwidth, RF communication quality, etc.) through communication quality information regarding the wireless channel.

In Operation S140, the processing unit 210 may determine a data resolution corresponding to transmission characteristics. In Operation S150, the processing unit 210 may convert electrocardiogram data according to a data resolution.

The processing unit 210 specifies the first correction scale or the first translation degree through a data resolution corresponding to transmission characteristics, and may wavelet-transform biosignals such as electrocardiogram data, etc. into the first correction scale or the first translation degree. At this time, the biosignals, such as electrocardiogram data, etc. can be decomposed into multiple frequency components. Further, the biosignal measuring apparatus 100 may decompose biosignals such as electrocardiogram data, etc. into a plurality of data sections, and each of a plurality of data sections can be converted into a bit scale. The bit scale may be determined by a pattern of the corresponding section. The biosignal measuring device 100 and the processing unit 210 may be electrically connected or connected through a network.

The processing unit 210 may designate the first bandwidth through a data resolution corresponding to transmission characteristics, and convert biosignals such as electrocardiogram data, etc. so as to raise, among the components of biosignals such as electrocardiogram data, etc. the resolution of the designated first bandwidth, and lower the resolution of the rest of the bandwidths, i.e. the second bandwidth. At this time, wavelet transformation may be used as a transformation method; however, not limited to this, various other methods are also available. On this occasion, biosignals such as electrocardiogram data, etc. can be decomposed into a plurality of frequency components based on bandwidths. Further, the biosignal measuring apparatus 100 may decompose biosignals such as electrocardiogram data, etc. into a plurality of data sections, and each of a plurality of data sections can be converted into a bit scale. The bit scale may be determined by a pattern of the corresponding section.

The processing unit 210 may decompose biosignals including electrocardiogram data, etc. into multiple data sections based on frequency components, data size, time intervals, etc. before converting the data by applying a data resolution.

In Operation S150, the processing unit 210 may convert electrocardiogram data according to a data resolution.

FIG. 4 illustrates a flowchart that converts electrocardiogram data according to a control signal. As illustrated in FIG. 4, in Operation S210, the biosignal measuring apparatus 100 senses biosignals such as electrocardiogram data, etc.

In Operation S220, the biosignal measuring apparatus 100 may establish a wireless channel with the data receiving device 200.

In Operation S230, the biosignal measuring apparatus 100 may receive communication control signals through a wireless channel.

In Operation S240, the biosignal measuring apparatus 100 may convert biosignals such as electrocardiogram data, etc. according to communication control signals from the data receiving device 200.

The processing unit 210 may calculate a set value corresponding to communication control signals including an output scale (e.g., an image resolution, etc.) of the data receiving device, and convert biosignals such as electrocardiogram data, etc. by applying a set value corresponding to communication control signals. At this time, a section where the aforementioned set value corresponding to the communication control signals is applied may be a part of the biosignals including electrocardiogram data, etc. designated by the communication control signals. The communication control signals may include an output scale value (i.e. image resolution value) based on a user input entered in the data receiving device or a section designated by user input.

In another embodiment, the communication control signals may include biometric parameters. The processing unit 210 may designate a data section using biometric parameters, and convert the data section by applying a set value included in the communication control signals. In such case, the data section designated based on biometric parameters may be a section in which abnormal biosignals are sensed, a section showing an abnormal heart rate, or a section in which an abnormal P wave is detected.

FIG. 5 illustrates a flowchart that converts electrocardiogram data according to data resolution when the data resolution corresponds to a transmission delay. As illustrated in FIG. 5, in Operation S310, the biosignal measuring apparatus 100 senses biosignals such as electrocardiogram data, etc.

In Operation S315, the biosignal measuring apparatus 100 establishes a wireless channel with the data receiving device 200 to transmit electrocardiogram data.

In Operation S320, the biosignal measuring apparatus 100 may receive feedback signals from the data receiving device 200.

In Operation S330, the biosignal measuring apparatus 100 detects whether a transmission delay is generated. In Operation S340, the processing unit 210 may determine a data resolution corresponding to a transmission delay, and convert electrocardiogram data according to the data resolution in the biosignal measuring apparatus 100. The biosignal measuring apparatus 100 may transmit a plurality of transmission data generated by conversion to the data receiving device 200 (Operation S350).

If no transmission delay is detected, the biosignal measuring apparatus 100 may transmit electrocardiogram data to the data receiving device 200 through a wireless channel (Operation S355).

Figure 6A:
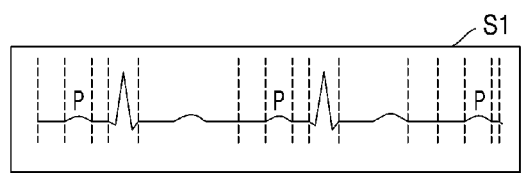
FIGS. 6A through 6C are diagrams illustrating processing of communication control signals received from a data receiving device, where.
Figure 6B:
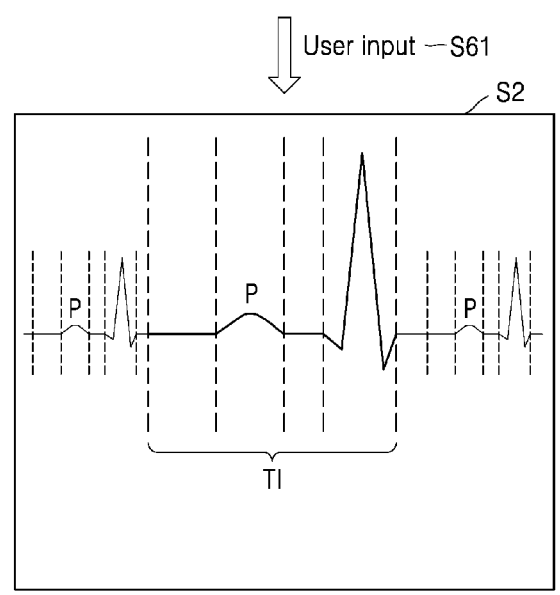
Figure 6C:
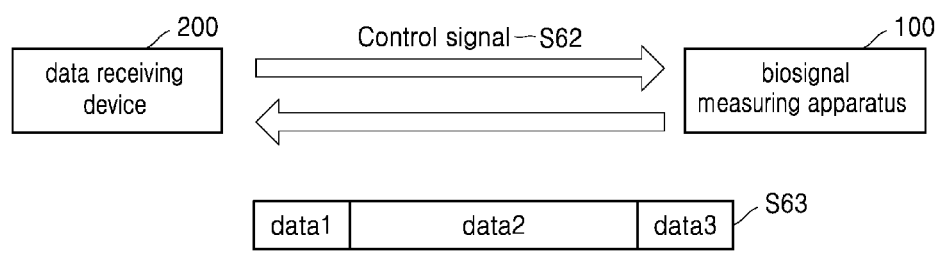

FIG. 6A through FIG. 6C are diagrams which illustrate processing of communication control signals received from the data receiving device.

In the data receiving device 200, biosignals received from the biosignal measuring apparatus 100 are output as in S1, as shown in FIG. 6A. User input S61 to expand TI section in S1 can be entered, as shown in FIG. 6B. When a user input S61 is entered, the communication control signals S62 corresponding to the user input are delivered to the biosignal measuring apparatus 100, as shown in FIG. 6C. Here, a user input generating communication control signals may modify output scales (i.e., change of size) of electrocardiogram data, etc. or perform translation of entire or parts of the electrocardiogram data, etc.

As shown in FIG. 6C, the biosignal measuring apparatus 100 may generate and transmit data to the data receiving device 200 by raising data resolution of a data section corresponding to TI (data 2) while lowering data resolution of the rest of data sections (data 1, data 3), in response to communication control signals S62.

Figure 7:
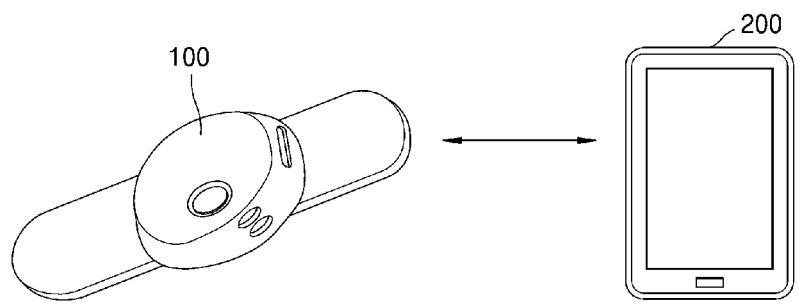
FIG. 7 is a diagram for explaining a network environment between a biosignal measuring apparatus and a data receiving device, according to embodiments of the present disclosure.
Figure 8:
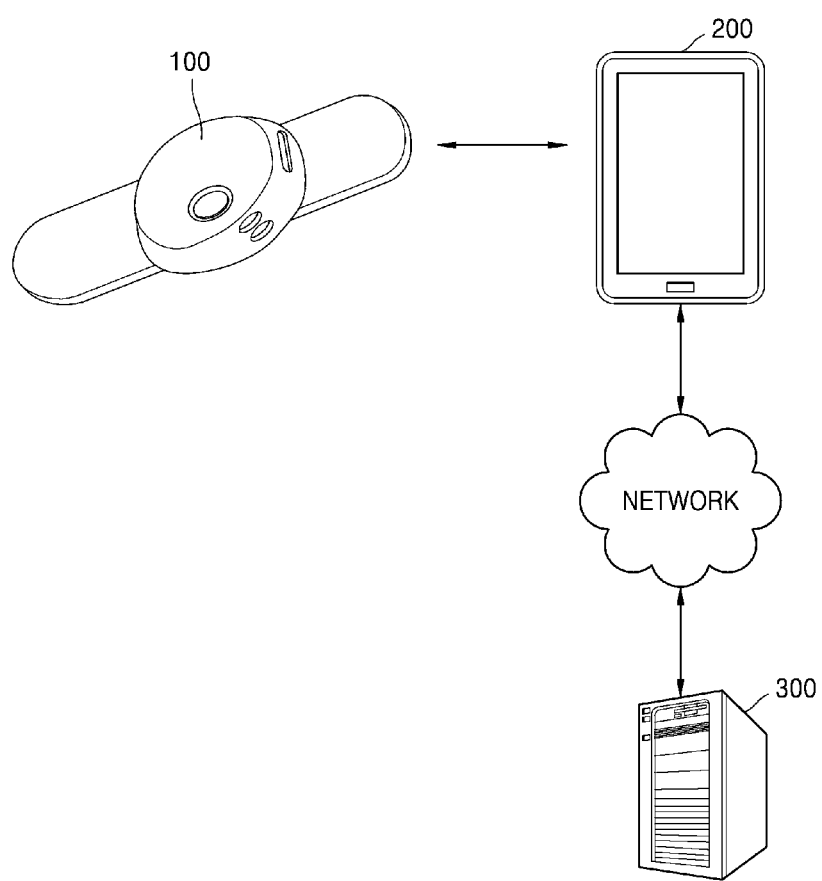
FIG. 8 is a diagram for explaining another network environment including an electrocardiogram management server.

FIG. 7 and FIG. 8 are diagrams for describing the operation of receiving and transmitting data between the biosignal measuring apparatus 100 and the receiving device 200 according to embodiments of the present disclosure.

The biosignal measuring apparatus 100 is attached onto a human body and may measure electrocardiogram data from one or more channels by means of multiple electrodes. The biosignal measuring apparatus 100 receives electrocardiogram measurement data from one or more channels, measured by external electrodes, and the number of electrocardiogram measurement channels can be increased. The biosignal measuring apparatus 100 may deliver electrocardiogram measured according to a predetermined cycle to the receiving device 200 in predetermined n units (transmission data). The data receiving device 200 can transmit communication control signals related to measurement, transmission, etc. of electrocardiogram data to the biosignal measuring apparatus 100.

The biosignal measuring apparatus 100 may convert biosignals including electrocardiogram data, etc. based on a data resolution of a communication environment, and transmit the converted result to the data receiving device 200.

The biosignal measuring apparatus 100 may determine a data resolution in consideration of status information on the power supply, status information on the data receiving device, etc., and convert electrocardiogram data by applying the determined data resolution. The data receiving device 200 receives electrocardiogram data from the biosignal measuring apparatus 100. If user input such as change in output scale, translation, etc. is entered, the data receiving device 200 may generate communication control signals corresponding the user input and transmit the same to the biosignal measuring apparatus 100.

The data receiving device 200 may include a module for restoring received electrocardiogram data. The data receiving device 200 may receive electrocardiogram data partially in case of increase of communication distance with the biosignal measuring apparatus 100, degradation in specification and communication performance of the data receiving device 200, degradation in communication performance of the biosignal measuring apparatus 100, etc., and restore electrocardiogram data from the received partial electrocardiogram data. The data receiving device 200 may transmit one or more packets including information on received times (i.e. reception complete time) of transmission data of electrocardiogram data to the biosignal measuring apparatus 100. The received time information may be measured by a timer of the data receiving device 200. The biosignal measuring apparatus 100 may determine a degree of transmission delay based on time information received from the data receiving device 200.

The data receiving device 200 can be used in small electronic devices, including a mobile phone, smart phone, laptop computer, digital broadcasting terminal, personal digital assistants (PDA), portable multimedia player (PDA), navigation, MP3 player, electric toothbrush, electronic tag, lighting system, remote control, etc. but not limited to the foregoing, it may also be used in a computing device having one or more processors, distributed computing device, server equipment, etc. The data receiving device 200 is described as an electronic device including a display; however, it may be a computing device without an output unit.

The data receiving device 200 may be implemented to receive electrocardiogram data from multiple biosignal measuring apparatuses 100. The data receiving device 200 may be implemented to include only one or more processors and memory. The operations of the data receiving device 200 may be carried out by executing a program stored in an internal memory.

As described in FIG. 8, the data receiving device 200 can restore electrocardiogram data received from the biosignal measuring apparatus 100 and transmit the electrocardiogram data to an electrocardiogram management server 300. Up to this point, the process of restoring electrocardiogram data has been described as being carried out at the data receiving device 200 for the sake of convenient explanation; however, it can be performed at the electrocardiogram management server 300. Moreover, it is also obvious that the biosignal measuring apparatus 100 may transmit electrocardiogram data directly to the electrocardiogram management server 300, allowing the data processing by the electrocardiogram management server 300.

The electrocardiogram management server 300 may manage electrocardiogram data from the data receiving device 200 in connection with objects. The electrocardiogram management server 300 may store electrocardiogram data of objects individually in association with accounts of each object.

In another embodiment, the biosignal measuring apparatus 100 may communicate with the data receiving device 200 through a repeater (not explicitly shown in the drawings).

Figure 9:
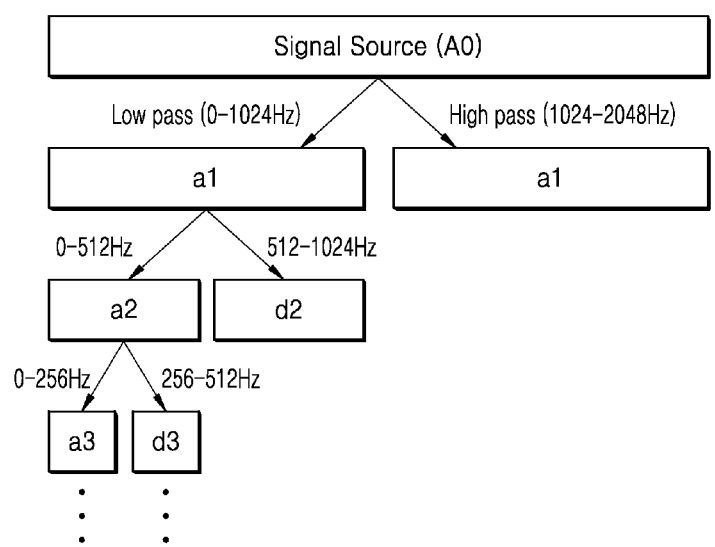
FIG. 9 is a diagram for explaining a process of wavelet transformation of electrocardiogram data.

FIG. 9 is a diagram for explaining the converting process of electrocardiogram data.

The biosignal measuring apparatus 100 may convert electrocardiogram data A0 into a1 and d1 based on, for example, the reference frequency of 1024 Hz. The biosignal measuring apparatus 100 may wavelet transform converted data units until a desired transmission data size is achieved. In this manner, a1, a portion of electrocardiogram data may be converted into a2 and d2, and further, a2 into a3 and d3.

Through such converting process, electrocardiogram data may be segmented into smaller data.

Figure 10:
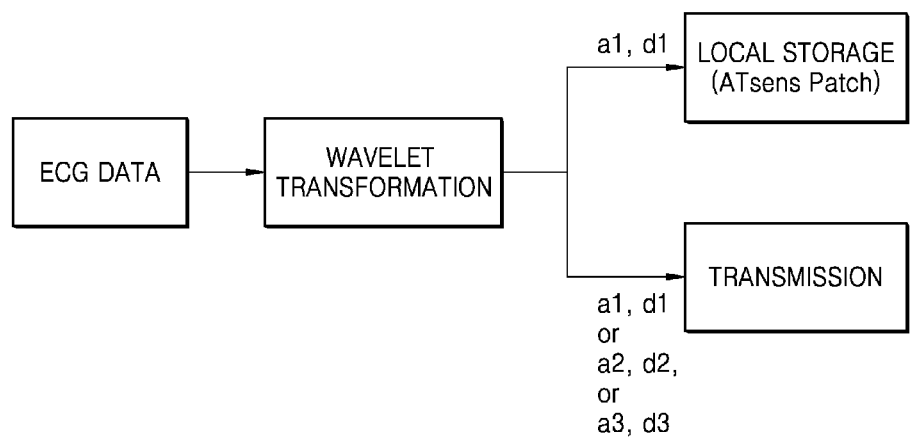
FIG. 10 is a diagram for explaining processing of electrocardiogram data according to a position where the electrocardiogram data is stored.

FIG. 10 is a diagram for explaining the processing of electrocardiogram data according to a position where the electrocardiogram data is stored.

The biosignal measuring apparatus 100 wavelet-transforms electrocardiogram data. The biosignal measuring apparatus 100 may store biosignals of unconverted electrocardiogram data (i.e. a1 and d1) in an internal memory, and transmit to an external receiving device one of a1 and d1, a2 and d2, and a3 and d3.

The devices described above may be implemented by hardware components, software components, and/or combinations of hardware components and software components. For example, the devices and components described in embodiments can be implemented by using one or more general purpose computers or special purpose computers, for example, a processor, controller, arithmetic logic unit (ALU), digital signal processor, microcomputer, field programmable gate array (FPGA), programmable logic unit (PLU), microprocessor, or any other device capable of executing and responding to instructions. The processing unit may run an operating system (OS) and one or more software applications executed in the operating system. In addition, the processing unit may also access, store, manipulate, process, and generate data in response to execution of software. Although some embodiments describe the use of single processing unit for the sake of convenience in understanding, a person with ordinary skill in the art can understand that a processing unit may include multiple processing elements and/or processing elements structured in a plural form. For example, the processing unit may include multiple processors, or one processor with one controller. In addition, other processing configurations, such as a parallel processor are also an option.

Software may include computer programs, codes, instructions, or combinations of at least one of the foregoing, and configure a processing unit to operate as desired, or command a processing unit independently or collectively. Software and/or data can be permanently or temporarily embodied in certain types of devices, components, virtual equipment, computer storage media or devices, or signal wave to be transmitted, to be interpreted by a processing unit or to provide commands or data to a processing unit. Software may be dispersed in a networked computer system, and stored or executed in a dispersed manner. Software and data may be stored in one or more computer readable recording media.

The method according to embodiments may be implemented in the form of a program instruction that can be performed through various computing means and recorded on a computer readable medium. The computer readable medium may include a program command, data file, data structure, etc. solely or in combination. The program instructions recorded in the medium may be specifically designed and configured for embodiments, or may be published for use to those skilled in computer software. Examples of computer readable recording media include magnetic medium such as a hard disk, floppy disc, and magnetic tape; optical media such as CD-ROM, and DVD; magneto-optical media such as floptical disk; and hardware device specifically configured to store and execute program instructions, such as ROM, RAM, flash memory, etc. Examples of program instructions not only include machine language codes, which are generated by a compiler, but advanced language codes that can be executed by a computer using an interpreter, etc. The aforementioned hardware device may be configured to serve as one or more software modules to perform the operations described in embodiments, and vice versa.

According to embodiments, electrocardiogram data can be converted in accordance with a data resolution corresponding to communication environments and transmission characteristics.

As described above, embodiments have been explained by limited illustrative examples and drawings, but a person with ordinary skill in the art to which the present disclosure pertains may make various modifications and revisions of embodiments based on the present disclosure. For example, a proper result may also be achieved even when the described techniques are performed in different orders than explained herein, and/or the described components including systems, structures, devices, circuits, etc. are combined or joined in a different manner than explained herein, or are replaced or substituted with other components or equivalents.

Therefore, other implementations and embodiments, as well as equivalents to the scope of the claims also fall within the scope of the claims to be described below.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A biosignal measuring apparatus for converting and transmitting biosignals, comprising:
    a communication unit configured to receive first electrocardiogram data of a user and establish a wireless communication channel with a data receiving device; and a processor system including a processor and coupled to the communication unit;
    a memory that stores executable instructions that, when executed by the processing system, facilitate performance of operations, the operations comprising:
    decompose the first electrocardiogram data into a plurality of data sections designated using time intervals of the first electrocardiogram data, wherein the plurality of data sections include a first data section and a second data section;
    determine real-time transmission characteristics based on communication quality information regarding the wireless communication channel by obtaining a feedback signal from the data receiving device through the wireless communication channel;
    determine first data resolution corresponding to the real-time transmission characteristics in response to a transmission delay being detected such that second electrocardiogram data is transmitted without a data loss under the real-time transmission characteristics of the wireless communication channel;
    convert the first data section into a first bit scale determined by a signal pattern of the first data section in response to the transmission delay occurred in the first data section by applying the first data resolution and not convert the second data section into a bit scale in response to no transmission delay occurred in the second data section, wherein the signal pattern corresponds to a periodic pattern included in the first data section; and
    transmit the second electrocardiogram data including the first bit scale representing the signal pattern of the first data section and the second data section to the data receiving device.

2. The biosignal measuring apparatus of claim 1, wherein the determining the real-time transmission characteristics further includes determining wireless bandwidths or radio frequency (RF) communication quality based on the communication quality information regarding the wireless communication channel.

3. The biosignal measuring apparatus of claim 1, wherein a size of the second electrocardiogram data is smaller than a size of the first electrocardiogram data by transmitting the first bit scale instead of the first data section.

4. The biosignal measuring apparatus of claim 1, wherein the operations further comprise:
    converting the first electrocardiogram data according to a communication control signal from the data receiving device.

5. The biosignal measuring apparatus of claim 4, wherein the operations further comprise transforming the first electrocardiogram data k times by wavelet transforming until a desired transmission data size is achieved.

6. The biosignal measuring apparatus of claim 1, wherein the operations further comprise storing the first electrocardiogram data in an internal memory.

7. A method of measuring biosignals for converting and transmitting the biosignals, the method comprising:
    receiving, by a biosignal measuring apparatus, first electrocardiogram data of a user;
    establishing, by the biosignal measuring apparatus, a wireless communication channel with a data receiving device;
    decomposing, by the biosignal measuring apparatus, the first electrocardiogram data sensed into a plurality of data sections designated using time intervals of the first electrocardiogram data, wherein the plurality of data sections includes a first data section and a second data section;
    determining, by the biosignal measuring apparatus, real-time transmission characteristics based on communication quality information regarding the wireless communication channel by obtaining a feedback signal from the data receiving device through the wireless communication channel;

determining, by the biosignal measuring apparatus, first data resolution corresponding to the real-time transmission characteristics in response to a transmission delay being detected such that second electrocardiogram data is transmitted without a data loss under the real-time transmission characteristics of the wireless communication channel;

converting, by the biosignal measuring apparatus, the first data section into a first bit scale determined by a signal pattern of the first data section in response to the transmission delay occurred in the first data section by applying the first data resolution and not converting the second data section into the first bit scale in response to no transmission delay occurred in the second data section, wherein the signal pattern corresponds to a periodic pattern included in the first data section; and transmitting, by the biosignal measuring apparatus, the second electrocardiogram data including the first bit scale representing the signal pattern of the first data section and the second data section to the data receiving device.

8. The method of measuring biosignals of claim 7, wherein the real-time transmission characteristics further includes wireless bandwidths or radio frequency (RF) communication quality, based on the communication quality information regarding the wireless communication channel.

9. The method of measuring biosignals of claim 7, wherein:
a size of the second electrocardiogram data is smaller than a size of the first electrocardiogram data by transmitting the first bit scale instead of the first data section.

10. The method of measuring biosignals of claim 7, further comprising
converting the first electrocardiogram data according to a communication control signal from the data receiving device.

11. The method of measuring biosignals of claim 10, further comprising transforming the first electrocardiogram data k times by wavelet transforming until a desired transmission data size is achieved.

12. The method of measuring biosignals of claim 7, further comprising storing the first electrocardiogram data in an internal memory.

* * * * *